(12) United States Patent
Park et al.

(10) Patent No.: US 9,801,973 B1
(45) Date of Patent: Oct. 31, 2017

(54) PEPTIDE HAVING ZIRCONIA-BINDING CAPACITY

(71) Applicants: SEOUL NATIONAL UNIVERSITY R&DB FOUNDATION, Seoul (KR); NANO INTELLIGENT BIOMEDICAL ENGINEERING CORPORATION CO. LTD, Chungcheongbuk-do (KR)

(72) Inventors: Yoon Jeong Park, Seoul (KR); Jin Sook Suh, Seoul (KR); Chong-Pyoung Chung, Seoul (KR); Jue-Yeon Lee, Gyeonggi-do (KR); Yeonsu Kim, Seoul (KR)

(73) Assignees: SEOUL NATIONAL UNIVERSITY R&DB FOUNDATION, Seoul (KR); NANO INTELLIGENT BIOMEDICAL ENGINEERING CORPORATION CO. LTD., Chungcheongbuk-do (KR)

( * ) Notice: Subject to any disclaimer, the term of this patent is extended or adjusted under 35 U.S.C. 154(b) by 0 days.

(21) Appl. No.: 15/504,035

(22) PCT Filed: Apr. 5, 2016

(86) PCT No.: PCT/KR2016/003505
§ 371 (c)(1),
(2) Date: Feb. 15, 2017

(87) PCT Pub. No.: WO2016/163711
PCT Pub. Date: Oct. 13, 2016

(30) Foreign Application Priority Data

Apr. 6, 2015  (KR) .................. 10-2015-0048441

(51) Int. Cl.
| | | |
|---|---|---|
| *A61K 38/00* | (2006.01) | |
| *A61L 27/04* | (2006.01) | |
| *C07K 19/00* | (2006.01) | |
| *C07K 7/08* | (2006.01) | |
| *A61L 27/00* | (2006.01) | |
| *C07K 7/00* | (2006.01) | |

(52) U.S. Cl.
CPC .............. *A61L 27/04* (2013.01); *C07K 7/08* (2013.01); *C07K 19/00* (2013.01); *A61L 27/00* (2013.01); *C07K 7/00* (2013.01)

(58) Field of Classification Search
None
See application file for complete search history.

(56) References Cited

U.S. PATENT DOCUMENTS

| | | |
|---|---|---|
| 6,280,760 B1 | 8/2001 | Meyer et al. |
| 2006/0068386 A1* | 3/2006 | Slesarev .............. C07K 14/195 435/6.18 |

FOREIGN PATENT DOCUMENTS

| | | |
|---|---|---|
| JP | 2009-007339 A | 1/2009 |
| KR | 10-2005-0119489 A | 12/2005 |
| KR | 10-1213355 B1 | 12/2012 |

OTHER PUBLICATIONS

Gnanasekar, M., et al, "Novel Phage Display-Based Subtractive Screening to Identify Vaccine Candidates of Brugia malayi", "Infection and Immunity", Aug. 2004, pp. 4707-4715, vol. 72, No. 8.
Hashimoto, K., et al., "Identification of peptide motif that binds to the surface of zirconia", "Dental Materials Journal", Nov. 2011, pp. 935-940, vol. 30, No. 6.
Nakamura, K, et al., "Zirconia as a Dental Implant Abutment Material: A Systematic Review", "The International Journal of Prosthodontics", 2010, pp. 299-309, vol. 23, No. 4.
Rothenstein, D., et al., "Generation of luminescence in biomineralized zirconia by zirconia-binding peptides", "CrystEngComm", Feb. 28, 2015, pp. 1783-1790, vol. 17, No. 8, Publisher: The Royal Society of Chemistry.

* cited by examiner

*Primary Examiner* — Thomas S Heard
(74) *Attorney, Agent, or Firm* — Hultquist, PLLC; Steven J. Hultquist

(57) ABSTRACT

The present invention relates to a peptide that binds specifically to the surface of zirconia, and more particularly, to a peptide conjugate obtained by linking a functional drug to the peptide so as to enable the drug to be securely fixed to the surface of zirconia to thereby maintain the activity of the drug over a long period of time. The zirconia-binding peptide according to the present invention can be securely fixed to the surface of zirconia so that the activity of a physiologically active substance introduced into the peptide can be maintained on the zirconia surface over a long period of time. Thus, the zirconia-binding peptide is useful for surgical regenerative treatment.

10 Claims, 2 Drawing Sheets

SEQUENCE LISTING

<160> NUMBER OF SEQ ID NOS: 7

<210> SEQ ID NO 1
<211> LENGTH: 12
<212> TYPE: PRT
<213> ORGANISM: Artificial Sequence
<220> FEATURE:
<223> OTHER INFORMATION: Zr-BP

<400> SEQUENCE: 1

Val Ser Pro Phe Gly Thr Lys Trp Ser Pro Phe Val

<210> SEQ ID NO 2
<211> LENGTH: 12
<212> TYPE: PRT
<213> ORGANISM: Artificial Sequence
<220> FEATURE:
<223> OTHER INFORMATION: Zr-BPC

<400> SEQUENCE: 2

Val Ser Ala Ala Gly Thr Lys Ala Ser Pro Ala Val
1               5                   10

<210> SEQ ID NO 3
<211> LENGTH: 12
<212> TYPE: PRT
<213> ORGANISM: Artificial Sequence
<220> FEATURE:
<223> OTHER INFORMATION: PL1

<400> SEQUENCE: 3

Ile Gly Asn Ser Phe Ser Phe Pro Ala Val Tyr Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: PL2

<400> SEQUENCE: 4

Leu Arg Leu Asp Val Asp Arg Ala Ile Ser Leu Leu
1               5                   10

<210> SEQ ID NO 5
<211> LENGTH: 36
<212> TYPE: DNA
<213> ORGANISM: Artificial Sequence
<220> FEATURE:
<223> OTHER INFORMATION: DNA encoding Zr-BP

<400> SEQUENCE: 5
gtgagtccgt tggtactaa gtggtctccg tttgtt                                  36

<210> SEQ ID NO 6
<211> LENGTH: 36
<212> TYPE: DNA
<213> ORGANISM: Artificial Sequence
<220> FEATURE:
<223> OTHER INFORMATION: DNA encoding PL1

<400> SEQUENCE: 6
attgggaata gttttttcttt tcctgcggtt tatagg                                 36

<210> SEQ ID NO 7
<211> LENGTH: 36
<212> TYPE: DNA
<213> ORGANISM: Artificial Sequence
<220> FEATURE:
<223> OTHER INFORMATION: DNA encoding PL2

<400> SEQUENCE: 7
ttgcggttgg atgttgatag ggctattagt ttgttg                                  36

PEPTIDE HAVING ZIRCONIA-BINDING CAPACITY

CROSS-REFERENCE TO RELATED APPLICATIONS

This application is a U.S. national phase under the provisions of 35 U.S.C. §371 of International Patent Application No. PCT/KR16/03505 filed Apr. 5, 2016, which in turn claims priority of Korean Patent Application No. 10-2015-0048441 filed Apr. 6, 2015. The disclosures of such international patent application and Korean priority patent application are hereby incorporated herein by reference in their respective entireties, for all purposes.

TECHNICAL FIELD

The present invention relates to a peptide that binds specifically to the surface of zirconia, and more particularly, to a peptide conjugate obtained by linking a functional drug to the peptide so as to enable the drug to be securely fixed to the surface of zirconia to thereby maintain the activity of the drug over a long period of time.

BACKGROUND ART

Implant materials to be implanted in vivo, particularly dental implant materials, are widely used as artificial teeth capable of replacing missing teeth to restore the masticatory function of some or all of the missing teeth. The success rate and long-term prognosis of implant treatment are influenced by the bone quantity and quality of the implant site in the patient, and depend on the stability of the implant. The stability of the implant can be divided into physical fixation that is obtained when the implant is brought into contact with the surrounding bone upon implant placement and biological fixation that results from the formation of new bone tissue around the implant and the occurrence of osseointegration in the surrounding bone after placement of the implant (Guideline for Evaluation of Zirconia Materials, the Korea Food & Drug Administration, 2011).

When an implant is placed in the alveolar bone of an adult patient, the stability of the implant is reduced while bone resorption for forming new bone in the existing bone occurs. However, while new bone is formed around the implant, the stability of the implant gradually increases again by osseointegration between the implant and the alveolar bone. However, in the case of elderly patients in whom it is difficult to ensure initial implant stability important for osseointegration, due to insufficient bone quantity or quality, early failure of the implant may occur, and if a load is applied to the implant having low initial stability, delayed osseointegration may be caused by micro-motion. Until now, to overcome such shortcomings, it has been attempted to increase initial implant stability by changing the length or diameter of the implant itself or treating the surface of the implant to increase the ability of the implant to adhere to osteocytes. However, it is still difficult to ensure initial implant stability after implant placement by such physical changes (Nakamura K et al., *International Journal of Prosthodontics* 23:299-309, 2010).

Thus, in the case of not only elderly patients having insufficient bone quality and quantity, but also general adult patients, it is essential to apply biological factors in order to promote initial osseointegration after implant placement and shorten the treatment period. Until now, a product obtained by chemically immobilizing a physiologically active substance on the surface of a dental implant has not yet been commercialized. However, in the case of apatite which is used as a synthetic material to increase bone quantity during implant placement, studies have been conducted on the use of apatite together with a physiologically active material such as extracellular matrix protein, tissue growth factor or bone morphogenetic protein. In addition, products such as GEM21S (containing PDGF), INFUSE (containing BMP-2) and the like, obtained by applying apatite together with a physiologically active substance or coating the surface of apatite with a physiologically active substance, have been developed. However, there are problems in that, after these products are implanted in vivo, the physiologically active substance is not securely fixed to the surface of the apatite material and is easily released from the surface of the apatite material so as to be degraded by exposure to systemic blood, and thus the physiological activity of the physiologically active substance can be reduced and the physiologically active substance can cause side effects in tissues other than the target tissue. For this reason, for tissue regeneration by an implant, it is required that a physiologically active substance be securely fixed to the surface of the implant biomaterial so that the effective activity thereof can be maintained over a long period of time (KR 10-1213355).

Accordingly, the present inventors have made extensive efforts to solve the above-described problems occurring in the prior art, and as a result, have identified a short peptide sequence having a strong binding affinity for the surface of an implant, and have found that the peptide easily binds to the surface of a zirconia implant and is maintained in a stable state, thereby completing the present invention.

SUMMARY OF THE INVENTION

It is an object of the present invention to provide a zirconia-binding peptide represented by the amino acid sequence of SEQ ID NO: 1, a peptide conjugate comprising a physiologically active peptide or physiologically active protein linked to the zirconia-binding peptide, and a biomaterial comprising the zirconia-binding peptide or the peptide conjugate.

To achieve the above objects, the present invention provides a zirconia-binding peptide represented by the amino acid sequence of SEQ ID NO: 1.

The present invention also provides a peptide conjugate comprising a physiologically active peptide or physiologically active protein linked to the above-described zirconia-binding peptide.

The present invention also provides a biomaterial comprising the above-described zirconia-binding peptide or the above-described peptide conjugate.

BEST MODE FOR CARRYING OUT THE INVENTION

Figure 1:
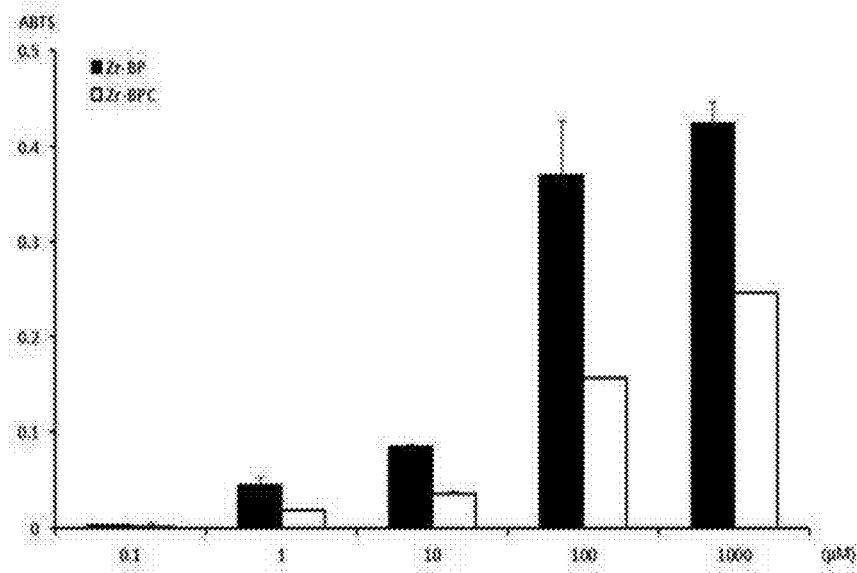
FIG. 1 shows the results of a binding assay performed using an avidin-biotin complex to measure the binding affinities of a zirconia-binding peptide sequence and a sequence of Comparative Example 1.

Unless defined otherwise, all technical and scientific terms used herein have the same meaning as commonly understood by one of ordinary skill in the art to which the invention pertains. Generally, the nomenclatures used herein are those well known and commonly employed in the art.

In the present invention, in order to securely fix a physiologically active substance to enable the activity thereof to be maintained over a long period of time, by use of a peptide linker capable of binding to the surface of a zirconia implant without chemical modification, a peptide sequence having a binding affinity for an implant made of zirconia was identified by a phage display technique, and it was found that the peptide can be present on the zirconia surface in a stable state.

In one aspect, the present invention is directed to a zirconia-binding peptide represented by the amino acid sequence of SEQ ID NO: 1.

In the present invention, the zirconia-binding peptide preferably binds to zirconia, which is used as a biomaterial, without chemical modification, but is not limited thereto.

In another aspect, the present invention is directed to a peptide conjugate comprising a physiologically active peptide or physiologically active protein linked to the zirconia-binding peptide.

In the present invention, the conjugate of the zirconia-binding peptide and the physiologically active peptide may be chemically synthesized using a peptide synthesizer. Specifically, a physiologically active domain may be chemically linked to the C- or N-terminus of the zirconia-binding peptide, thereby synthesizing a zirconia binding peptide-physiologically active peptide (e.g., osteogenic differentiation-inducing sequence) conjugate consisting of N terminus-zirconia binding peptide-physiologically active domain-C terminus or N terminus-physiologically active domain-zirconia binding peptide-C terminus.

The physiologically active domain which is a peptide is a substance that has osteogenic differentiation-inducing activity or anti-inflammatory activity required for implant placement and that regulates gene expression and physiological function in vitro or in vivo. This physiologically active domain which is a peptide may act as a controlling agent when a substance that is involved in functional regulation in vivo is deficient or when abnormal pathology caused by excessive secretion appears. It may be an L- or D-form in view of its stability in vivo.

In the present invention, the physiologically active peptide is preferably selected from the group consisting of anti-inflammatory, anti-microbial, cell adhesion, bone tissue regeneration, and cell migration functional peptides, but is not limited thereto.

In the present invention, the physiologically active protein is preferably selected from the group consisting of a tissue regeneration factor, a tissue growth factor, an intracellular transcription factor, an extracellular matrix proteins, and an anti-inflammatory protein, but is not limited thereto.

In the present invention, a conjugate of the zirconia-binding peptide with a physiologically active peptide or a low-molecular substance can be formed by inducing chemical bonding using a crosslinking agent. If chemical bonding is induced using a crosslinking agent, the conjugate will be easily formed by the crosslinking agent, because the N-terminus of the zirconia-binding peptide has a free amino group.

Examples of a cross-linking agent that can be used in the present invention include, but not limited to, 1,4-bis-maleimidobutane (BMB), 1,11-bismaleimidotetraethyleneglycol (BM[PEO]4), 1-ethyl-3-[3-dimethyl aminopropyl] carbodiimide hydrochloride (EDC), succinimidyl-4-[N-maleimidomethylcyclohexane-1-carboxy-[6-amidocaproate]] (SMCC) and its sulfonate (sulfo-SMCC), succimidyl 6-[3-(2-pyridyldithio)-ropionamido] hexanoate (SPDP) and its sulfonate (sulfo-SPDP), m-maleimidobenzoyl-N-hydroxysuccinimide ester (MBS) and its sulfonate (sulfo-MBS), and succinimidyl [4-(p-maleimidophenyl) butyrate] (SMPB) and its sulfonate (sulfo-SMPB).

In another aspect, the present invention is directed to a biomaterial comprising the zirconia-binding peptide or the peptide conjugate.

In the present invention, the biomaterial is preferably an implant for in-vivo transplantation, which is made of a metal whose surface is coated with zirconia, a natural polymer, a synthetic polymer, and zirconia, but is not limited thereto.

In the present invention, zirconia is preferably a tetragonal material obtained by adding 3-5 wt % of a stabilizer to pure zirconium oxide, but is not limited thereto.

In the present invention, the natural polymer is preferably any one selected from the group consisting of collagen, alginic acid, propylene glycol alginic acid, chondroitin sulfate, and chitosan, but is not limited thereto. In addition, the synthetic polymer is preferably any one selected from the group consisting of polylacticglycolic acid, poloxamer, and propylene glycol, but is not limited thereto.

When a zirconia-coated metal, a natural polymer, a synthetic polymer and a dental or orthopedic implant are implanted in vivo, a physiologically active substance can be covalently bonded with the peptide without inducing chemical bonding so that it can be present in a stable state while the activity thereof can be maintained. Namely, the migration, proliferation and differentiation of bone tissue regeneration-associated cells around the implant will be promoted, and eventually an efficient tissue regeneration effect can occur within a short time so that the treatment time can be shortened. In addition, side effects on the whole body or other tissues, which can be induced due to an unstable bond on the implant surface, can be reduced. Thus, the implant is useful for surgical regenerative treatment.

As used herein, the term "implant" refers to a surgical material or procedure that is used to implant a biocompatible material into a defective area by an additional surgical operation such as bone grafting or distraction osteogenesis to thereby restore the function of the defective area. The defective area enters a regular regeneration stage after osseointegration that is the physiological, morphological and direct bonding of the placed implant body surface to the surrounding tissue whose normal function is maintained.

As used herein, the term "zirconia" generally refers to zirconium oxide ($ZrO_2$). Zirconia has advantages in that it has good biocompatibility and can induce high osseointegration after initial implant placement, because it increases calcium ions through ion exchange and increases cellular mobility to thereby increase the adhesion of the zirconia to bone.

Pure titanium that is currently widely used as an implant material has a problem in that it can show metal allergic reactions, or has a disadvantage in that bacteria are highly likely to adhere thereto. For this reason, in the case of patients with reduced immunity, the application of an implant made of another biocompatible material should be taken into consideration. In recent years, it was reported that a ceramic implant made of zirconia that is used as a substituent for titanium has excellent biocompatibility, shows the highest mechanical strength among ceramic materials, can resist rapid temperature changes, and has excellent aesthetic properties. Due to such advantages, zirconia is widely used as a material for artificial teeth.

In the present invention, a new phage display technique, named "subtractive panning", was additionally used to exclude the possibility of selecting a sequence that binds materials other than the zirconia disc surface.

As used herein, the term "subtractive panning" refers to a phage display technique which may be used to identify a sequence that binds to a specific material without binding to other specific materials. In the subtractive panning technique, a phage library is applied to a material that does not want to bind, and unbound phages are recovered, after which the phages are applied to a material that wishes to bind, and then unbound phages are discarded, and bound phages are recovered (Munirathinam, Gnanasekar et. al., Novel Phage Display-Based Subtrative Screening To Identify Vaccine Candidates of *Brugia malayi*, *Infect Immun.*, 72:4707-4715, 2004).

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1: Identification of Zirconia-Binding Peptide Sequence Using Phage Display To identify a specific peptide sequence that binds to the zirconia disc surface, a phage display technique was used. M13 phages labeled with a random peptide library with high diversity and complexity were applied to the zirconia disc surface, after which unbound phages were washed out, and bound phages were recovered. These procedures were repeated several times. A subtractive panning procedure was additionally used, and the DNA sequence of a peptide bound to the finally obtained phage was analyzed, thereby identifying a zirconia-binding peptide sequence. The subtractive panning is a new phage display technique which may be used to identify a sequence that binds to a specific material without binding to other specific materials.

In this Example, polystyrene plate wells were used to identify a zirconia-binding peptide through phage display, and thus this technique was applied to exclude sequences that bind to the polystyrene plate in addition to the zirconia disc surface.

TABLE 1

| Clone | DNA sequence | Amino acid sequence |
|---|---|---|
| #1 | 5'-GTG AGT CCG TTT GGT ACT AAG TGG TCT CCG TTT GTT-3' (SEQ ID NO: 5) | VSPFGTKWSPFV (SEQ ID NO: 1) |
| #2 | 5'-GTG AGT CCG TTT GGT ACT AAG TGG TCT CCG TTT GTT-3' (SEQ ID NO: 5) | VSPFGTKWSPFV (SEQ ID NO: 1) |
| #3 | 5'-GTG AGT CCG TTT GGT ACT AAG TGG TCT CCG TTT GTT-3' (SEQ ID NO: 5) | VSPFGTKWSPFV (SEQ ID NO: 1) |

TABLE 1-continued

| Clone | DNA sequence | Amino acid sequence |
|---|---|---|
| #4 | 5'-GTG AGT CCG TTT GGT ACT AAG TGG TCT CCG TTT GTT-3' (SEQ ID NO: 5) | VSPFGTKWSPFV (SEQ ID NO: 1) |
| #5 | 5'-GTG AGT CCG TTT GGT ACT AAG TGG TCT CCG TTT GTT-3' (SEQ ID NO: 5) | VSPFGTKWSPFV (SEQ ID NO: 1) |
| #6 | 5'-GTG AGT CCG TTT GGT ACT AAG TGG TCT CCG TTT GTT-3' (SEQ ID NO: 5) | VSPFGTKWSPFV (SEQ ID NO: 1) |
| #7 | 5'-GTG AGT CCG TTT GGT ACT AAG TGG TCT CCG TTT GTT-3' (SEQ ID NO: 5) | VSPFGTKWSPFV (SEQ ID NO: 1) |
| #8 | 5'-GTG AGT CCG TTT GGT ACT AAG TGG TCT CCG TTT GTT-3' (SEQ ID NO: 5) | VSPFGTKWSPFV (SEQ ID NO: 1) |
| #9 | 5'-GTG AGT CCG TTT GGT ACT AAG TGG TCT CCG TTT GTT-3' (SEQ ID NO: 5) | VSPFGTKWSPFV (SEQ ID NO: 1) |
| #10 | 5'-GTG AGT CCG TTT GGT ACT AAG TGG TCT CCG TTT GTT-3' (SEQ ID NO: 5) | VSPFGTKWSPFV (SEQ ID NO: 1) |
| #11 | 5'-GTG AGT CCG TTT GGT ACT AAG TGG TCT CCG TTT GTT-3' (SEQ ID NO: 5) | VSPFGTKWSPFV (SEQ ID NO: 1) |
| #12 | No insert | N/A |
| #13 | 5'-GTG AGT CCG TTT GGT ACT AAG TGG TCT CCG TTT GTT-3' (SEQ ID NO: 5) | VSPFGTKWSPFV (SEQ ID NO: 1) |
| #14 | 5'-GTG AGT CCG TTT GGT ACT AAG TGG TCT CCG TTT GTT-3' (SEQ ID NO: 5) | VSPFGTKWSPFV (SEQ ID NO: 1) |
| #15 | 5'-GTG AGT CCG TTT GGT ACT AAG TGG TCT CCG TTT GTT-3' (SEQ ID NO: 5) | VSPFGTKWSPFV (SEQ ID NO: 1) |
| #16 | 5'-GTG AGT CCG TTT GGT ACT AAG TGG TCT CCG TTT GTT-3' (SEQ ID NO: 5) | VSPFGTKWSPFV (SEQ ID NO: 1) |

It was revealed that clone #12 had no insert by DNA sequencing. However, other fifteen clones indicate identical sequences, VSPFGTKWSPFV It was revealed that clone #12 had no insert by DNA sequencing. However, other fifteen clones indicate identical sequences; VSPFGTKWSPFV.

After completion of repeated cycles of the above-mentioned conventional phage display, the resulting phages were amplified again and added to empty wells of a polystyrene plate, and then phages not bound to the well surface were recovered. Then, the recovered phages not bound to the polystyrene plate were bound once more to the zirconia disc surface, and then washed strongly with washing buffer, and only the remaining bound phages were finally recovered.

The phage display kit used was Ph.D.-12 Phage Display Kit purchased from New England Biolabs (USA). The kit contains phages labeled with a random peptide library consisting of 12 amino acids, 16 final clones screened using the kit were sent to Cosmogenetech Co., Ltd. (Korea) in an *E. coli* culture state to analyze the sequences thereof.

As a result, as can be seen in Table 1 above, 15 clones had the same DNA sequence, and the final peptide sequence Zr-BP (VSPFGTKWSPFV; SEQ ID NO: 1) consisting of 12 amino acid residues could be obtained by translation of the DNA sequence. Because the peptide sequence is highly likely to be a specific sequence that binds to the zirconia disc surface, the peptide sequence was selected as a specific peptide sequence candidate that binds to the zirconia disc surface.

Example 2: Synthesis of Zirconia-Binding Peptide

Peptides represented by SEQ ID NOs: 1 to 4 were synthesized from the C-terminus to the N-terminus by an F-moc solid-phase synthesis method using a synthesizer. Specifically, the peptides were synthesized using Rink resin (0.075 mmol/g, 100~200 mesh, 1% DVB crosslinking) having Fmoc-(9-fluorenylmethoxycarbonyl) as a blocking group linked thereto. 50 mg of Rink resin was placed in a synthesizer, and then swollen with DMF, after which the Fmoc-group was removed using a 20% piperidine/DMF solution. A 0.5M amino acid solution (solvent: dimethylformamide, DMF) according to the sequence from the C-terminus to the N-terminus, 1.0M DIPEA (dimethylformamide & N-methylpyrrolidone, DMF & NMP) and 0.5M HBTU (solvent: dimethylformamide, DMF) were added to the resin in amounts of 5, 10 and 5 equivalents, respectively, and allowed to react for 1-2 hours under a nitrogen atmosphere. After completion of each of the deprotection and coupling steps, the resin was washed twice with DMF and NMP. Even after coupling of the final amino acid, the resin was deprotected to remove the Fmoc-group.

Synthesis of the peptides was confirmed using a ninhydrin test method. The synthesized and tested resin was dried with tetrahydrofuran (THF) or dichloromethane (DCM), and then a trifluoroacetic acid (TFA) cleavage cocktail was added to the resin in an amount of 20 ml per g of the resin, followed by shaking for 3 hours. Next, the cocktail containing the resin and peptide dissolved therein was separated by filtration. Cold ether was added after removing the filtered out solution using a rotary evaporator or an excess amount of cold ether was added directly to the TFA cocktail solution containing the peptide dissolved therein, so as to crystallize the peptide in a solid phase. The crystallized peptide was isolated by centrifugation. At this time, the TFA cocktail was completely removed by washing several times with ether and a centrifugation process. The peptides thus obtained were dissolved in distilled water and freeze-dried.

Each of the synthesized peptides was cut from the resin, washed, freeze-dried, and then purified by liquid chromatography. The molecular weights of the purified peptides were measured by mass spectrometry.

Comparative Example 1: Synthesis of Zr-BPC Peptide (VSAAGTKASPAV; SEQ ID NO: 2)

Zr-BPC (VSAAGTKASPAV; SEQ ID NO: 2) wherein phenylalanine at $2^{nd}$ and $9^{th}$ positions, tryptophan at $5^{th}$ position and proline at $10^{th}$ position from the C-terminus in the sequence of SEQ ID NO: 1 are substituted with alanine was synthesized by an F-moc solid-phase synthesis method using a peptide synthesizer.

Comparative Example 2: Synthesis of Peptide that Binds to the Surface of Empty Well Containing No Zirconia Disc Through phage display, a 12-amino acid peptide sequence that binds to the surface of an empty well containing no zirconia disc was screened. Four clones were sent to Cosmogenetech Co., Ltd. (Korea) in an *E. coli* culture state to analyze the sequences thereof.

As a result, as shown in Table 2 below, two of the four clones had specific DNA sequences. The two DNA sequences were translated to obtain peptides PL1 (IGNSFSFPAVYR; SEQ ID NO: 3) and PL2 (LRLDVDRAISLL; SEQ ID NO: 4), each consisting of 12 amino acids. The peptides were synthesized by an F-moc solid-phase synthesis method using a peptide synthesizer.

TABLE 2

| Clone | DNA sequence | Amino acid sequence |
| --- | --- | --- |
| #1 | No insert | N/A |
| #2 | 5'-ATT GGG AAT AGT TTT TCT TTT CCT GCG GTT TAT AGG-3' (SEQ ID NO: 6) | IGNSFSFPAVYR (SEQ ID NO: 3) |
| #3 | 5'-TTG CGG TTG GAT GTT GAT AGG GCT ATT AGT TTG TTG-3' (SEQ ID NO: 7) | LRLDVDRAISLL (SEQ ID NO: 4) |
| #4 | No insert | N/A |

It was revealed that clone #1 and #4 had no insert by DNA sequencing.

Example 3: Binding Affinity of Zirconia-Binding Peptide 3-1: Synthesis of Zirconia-Binding Peptide Labeled with Biotin In order to examine the binding affinities of the peptides synthesized in Example 1 and Comparative Examples 1 and 2, the peptides were labeled with biotin. Each of the synthesized peptide domains was biotinylated using EZ-Link Sulfo-NHS-Biotin (Pierce Biotechnology, USA) according to the manufacturer's instruction, and unbound byproducts were removed by ultrafiltration that is a membrane separation method based on a pressure difference. The molecular weights of the synthesized products were measured by mass spectrometry. The synthesized products were analyzed and purified by reverse phase liquid chromatography. For analysis, a $C_{18}$ column having a diameter of 4.6 mm was used, and 0.1% TFA/H$_2$O and 0.092% TFA/acetonitrile were flushed onto the column at a rate of 1 ml/min with a gradient of 0-60% for 30 minutes. The wavelength of the UV detector used was 220 nm. For purification, a column having a diameter of 2.2 cm was used, and a flow rate of 20 ml/min and the solvent and detection wavelength as described above were used. Only the biotin-labeled peptide fraction was collected, and concentrated using a rotary evaporator to remove the solvent, followed by freeze-drying.

3-2: Measurement of Binding Affinity of Zirconia-Binding Peptide

To measure the binding affinity of the zirconia-binding peptide, a binding assay using an avidin-biotin complex was performed. Specifically, one zirconia disc was placed in each well of a 12-well polystyrene plate, and then blocked with a blocking buffer (0.1 M NaHCO$_3$ (pH 8.6), 5 mg/ml BSA, 0.02% NaN$_3$ (optional), filter sterilize) for at least one hour. Next, the blocking buffer was discarded, and each zirconia disc was strongly washed six times or more with a washing buffer (TBS+0.1% [v/v] Tween-20), after which 200 µl of each of the zirconia-binding peptide Zr-BP (SEQ ID NO: 1) of Example 1 and the peptides Zr-BPC (SEQ ID NO: 2), PL1 (SEQ ID NO: 3) and PL2 (SEQ ID NO: 4) of Comparative Examples 1 and 2, which were biotin-labeled, synthesized, separated and purified in Example 3-1, was dispensed to the surface of each zirconia disc at a concentration ranging from 100 nM to 1 µM. Each zirconia disc was incubated at room temperature for 15 hours, and then washed strongly with a washing buffer, and 200 µl of a 1:500 dilution of ExtrAvidin-peroxidase (Cat. #E2886, Sigma-Aldrich, USA) in a blocking buffer was dispensed to the surface of each zirconia disc. Each zirconia disc was incubated at room temperature for 1 hour, and then washed strongly with a washing buffer, after which 200 µl of a substrate solution (2,2'-AZINO-BIS, Cat. #A3219, Sigma-Aldrich, USA) was dispensed to the surface of each zirconia disc and allowed to react at room temperature for 20 minutes so as to develop color. Each zirconia disc was treated with 200 µl of 1% SDS solution to stop the reaction, and the absorbance at 405 nm was measured.

As a result, as can be seen in FIG. 1, when each zirconia disc was treated with each of the zirconia-binding peptide Zr-BP (SEQ ID NO: 1) of Example 1 and the peptide Zr-BPC (SEQ ID NO: 2) of Comparative Example 1, the absorbance value of the zirconia-binding peptide Zr-BP of Example 1 was higher than that of the peptide Zr-BPC of Comparative Example 1, and this increase in absorbance value was concentration-dependent. This demonstrates that the zirconia-binding peptide sequence is a sequence that binds to the zirconia disc surface in a concentration-dependent manner. In addition, such results suggest that the peptide sequence has a binding motif, although the binding affinity thereof is reduced due to the substitution of some amino acids with alanine.

Figure 2:
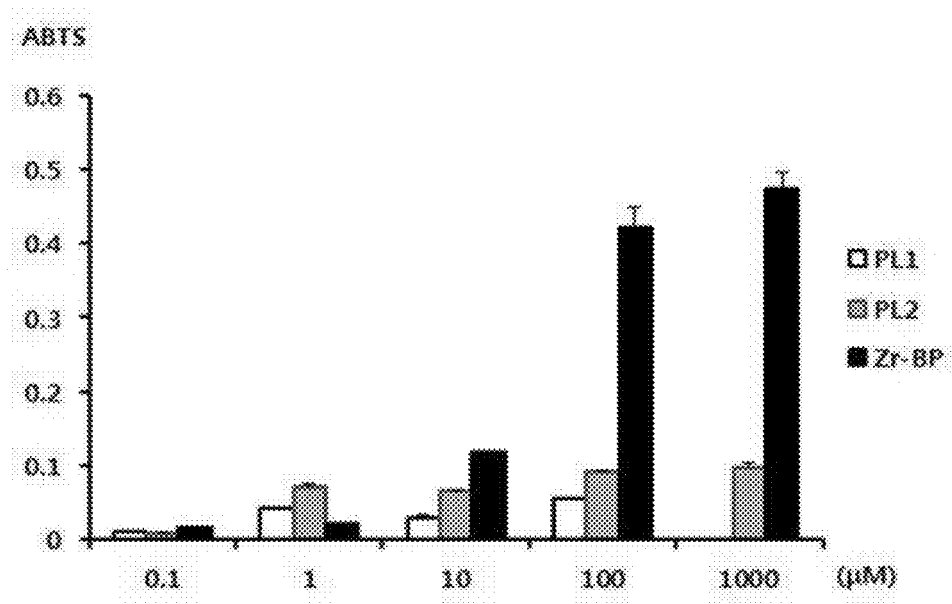
FIG. 2 shows the results of a binding assay performed using an avidin-biotin complex to measure the binding affinities of a zirconia-binding peptide sequence and sequences of Comparative Examples 2 and 3.

As shown in FIG. 2, when each zirconia disc was treated with each of the zirconia-binding peptide Zr-BP (SEQ ID NO: 1) of Example 1 and the peptides PL1 (SEQ ID NO: 3) and PL2 (SEQ ID NO: 4) of Comparative Example 2, the absorbance value of the zirconia-binding peptide Zr-BP of Example 1 was higher than those of the peptides (PL1 and PL2) of Comparative Example 2, and this increase in absorbance value was concentration-dependent. The peptides (PL1 and PL2) of Comparative Example 2 showed absorbance values independent of the concentration thereof, indicating that the peptide sequences of Comparative Example 2 do not bind to the zirconia disc surface.

Example 4: Examination of Maximum Binding Amount of Zirconia-Binding Peptide

To examine the maximum binding amount of the zirconia-binding peptide Zr-BP (SEQ ID NO: 1) per unit area of the zirconia disc surface, a binding assay using a avidin-biotin complex was performed. Specifically, one zirconia disc was placed in each well of a 12-well polystyrene plate, and then blocked with a blocking buffer (0.1 M $NaHCO_3$ (pH 8.6), 5 mg/ml BSA, 0.02% $NaN_3$ (optional), filter sterilize) for at least one hour. Next, the blocking buffer was discarded, and each zirconia disc was strongly washed six times or more with a washing buffer (TBS+0.1% [v/v] Tween-20), after which 200 µl of each of the zirconia-binding peptide Zr-BP (SEQ ID NO: 1) of Example 1 and the peptides Zr-BPC (SEQ ID NO: 2), PL1 (SEQ ID NO: 3) and PL2 (SEQ ID NO: 4) of Comparative Examples 1 and 2, which were biotin-labeled, synthesized, separated and purified in Example 3-1, was dispensed to the surface of each zirconia disc at a concentration ranging from 100 nM to 40 mM. Each zirconia disc was incubated at room temperature for 15 hours, and then washed strongly with a washing buffer, and 200 µl of a 1:500 dilution of ExtrAvidin-peroxidase (Cat. #E2886, Sigma-Aldrich, USA) in a blocking buffer was dispensed to the surface of each zirconia disc. Each zirconia disc was incubated at room temperature for 1 hour, and then washed strongly with a washing buffer, after which 200 µl of a substrate solution (2,2'-AZINO-BIS, Cat. #A3219, Sigma-Aldrich, USA) was dispensed to the surface of each zirconia disc and allowed to react at room temperature for 20 minutes so as to develop color. Each zirconia disc was treated with 200 µl of 1% SDS solution to stop the reaction, and the absorbance at 405 nm was measured.

Figure 3:
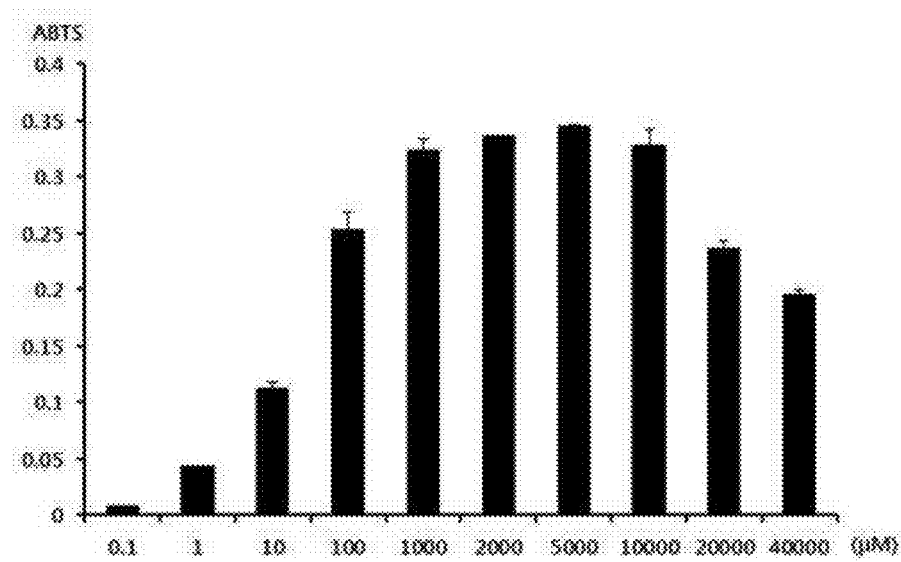
FIG. 3 shows the results of a binding assay performed using an avidin-biotin complex to measure the maximum amount of zirconia-binding peptide sequence bound to the zirconia disc surface.
Figure 3:
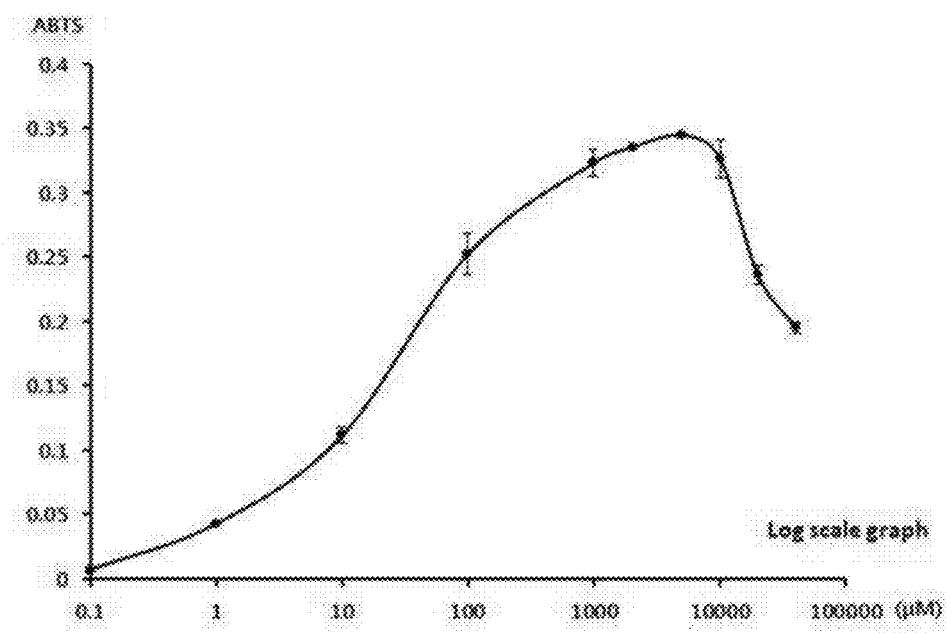

As a result, as can be seen in FIG. 3, the zirconia-binding peptide Zr-BP (SEQ ID NO: 1) showed the maximum absorbance value at a concentration of 2 mM. Absorbance changes appearing at a concentration of 10 mM or higher are believed to be false-negative results that can be explained by the high-dose hook effect. Based on the back-calculation from the molecular weight and dispensing amount of the zirconia-binding peptide, it can be seen that the maximum amount of zirconia-binding peptide bound to the surface of one zirconia disc is 622.8 µg. Thus, it can be seen that, because the diameter of the zirconia disc is 15.5 mm, about 3.3 µg of the zirconia-binding peptide can be fixed per $mm^2$ of the zirconia disc surface.

INDUSTRIAL APPLICABILITY

The zirconia-binding peptide according to the present invention can be securely fixed to the surface of zirconia so that the activity of a physiologically active substance introduced into the peptide can be maintained on the zirconia surface over a long period of time. Thus, the zirconia-binding peptide is useful for surgical regenerative treatment.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

The invention claimed is:
1. A zirconia-binding peptide represented by the amino acid sequence of SEQ ID NO: 1.
2. The zirconia-binding peptide of claim 1, wherein the zirconia-binding peptide binds to zirconia without chemical modification.
3. A peptide conjugate comprising a physiologically active peptide or physiologically active protein linked to the zirconia-binding peptide of claim 1.
4. The peptide conjugate of claim 3, wherein the physiologically active peptide is selected from the group consisting of anti-inflammatory, anti-microbial, cell adhesion, bone tissue regeneration, and cell migration functional peptides.
5. The peptide conjugate of claim 3, wherein the physiologically active protein is selected from the group consisting of a tissue regeneration factor, a tissue growth factor, an intracellular transcription factor, an extracellular matrix protein, and an anti-inflammatory protein.
6. A biomaterial comprising the zirconia-binding peptide represented by the amino acid sequence of SEQ ID NO: 1, or a peptide conjugate comprising a physiologically active peptide or physiologically active protein linked to the zirconia-binding peptide represented by the amino acid sequence of SEQ ID NO: 1.
7. The biomaterial of claim 6, wherein the biomaterial is an implant for in-vivo transplantation, which is made of a metal whose surface is coated with zirconia, a natural polymer, a synthetic polymer, and zirconia.
8. The biomaterial of claim 7, wherein zirconia is a tetragonal material obtained by adding 3-5 wt % of a stabilizer to pure zirconium oxide.
9. The biomaterial of claim 7, wherein the natural polymer is any one selected from the group consisting of collagen, alginic acid, propylene glycol alginic acid, chondroitin sulfate, and chitosan.
10. The biomaterial of claim 7, wherein the synthetic polymer is any one selected from the group consisting of polylacticglycolic acid, poloxamer, and propylene glycol.

* * * * *